United States Patent

Plant Pat. 3,939

Patented Aug. 10, 1976

3,939

*PASPALUM VAGINATUM* GRASS PLANT

Hubert F. Whiting 81-301 Avenue 50,
Indio, Calif. 92201

Filed Sept. 29, 1975, Ser. No. 617,588
Int. Cl.[2] A01H 5/00

U.S. Cl. Plt.—88 1 Claim

The present invention and discovery relates to a new and distinct variety of *Paspalum vaginatum* grass which was discovered by me growing under cultivation on a grass bowling green bank located at Adelaide, South Australia, Australia. Adelaide is on a coastal area, non-arid and about 35° south latitude.

I observed that this new variety had a greater density than other *Paspalum vaginatum* growing in the same geographical area. The uniformity and green color of the new variety was noticeably better, also a slightly deeper blue green than other *Paspalum vaginatum* grass in this area. At the time of year September, in Adelaide, during which the new variety was observed, the new variety of grass did not produce seed heads when mown. The absence or virtual absence of seed heads is a very desirable feature for turf grass usage.

I removed several pieces of stolons and rhizomes from the discovered new variety of *Paspalum vaginatum* grass. The pieces of stolons and rhizomes were transplanted in a nursery at the Royal Canberra Golf Course in Canberra, Australia. As these pieces grew, I broke off stolons and replanted them so as to cover a larger area. During this experiment I discovered that this new variety spread and covered much faster than the other *Paspalum vaginatum* grass.

Following the experiments described above, stolons of this new variety were planted at a sod farm located at Indio, Calif., about 34° north latitude. Indio is an arid desert area, with sandy slightly alkaline soil. The stolons were planted on 18 inch centers and produced complete cover in 40–50 days. Other *Paspalum vaginatum* grass planted in similar manner in the test area did not produce ground cover as rapidly as the new variety. During the next winter months at Indio I discovered that the new variety of *Paspalum vaginatum* grass kept its green color longer than the other *Paspalum vaginatum* grass by approximately 18 days. It appeared to have more resistance to lower temperatures, that is, about 40–50° F. As the cold nights gave way to slightly warmer spring weather, the new variety of *Paspalum vaginatum* grass began to acquire its green color more rapidly than the other *Paspalum vaginatum* grass.

As the new variety grass came back to its original deep green color, I began mowing the new variety grass and the other *Paspalum vaginatum* grass in the test area at ⅜ inch height. The new variety grass produced a superior turf grass surface with greater density and uniformity than other *Paspalum vaginatum* grass growing in the test area although the texture of the new variety grass was not quite as fine as the other *Paspalum vaginatum* grass. The difference in texture is particularly evidenced in regularly mown grass, the new variety grass producing blades slightly wider than the other *Paspalum vaginatum* grass under mown conditions. After several months had passed, about early summer, I removed some sod pieces for sod forming comparisons and I discovered that the new variety grass produced a greater density of root system than the other *Paspalum vaginatum grass*. In additional tests the new variety grass provided superior sod due to the superior root development, that is, the sod maintained its dimensional stability and integrity during handling. The new variety grass in the test area continued to produce a dense and very uniform turf grass surface very desirable for all general turf grass usage. During testing, the new variety grass and the other *Paspalum vaginatum* grass were regularly watered in the same manner and time. When watering was withheld from both grasses under the same conditions, the new variety grass kept its green appearance longer than said other grass and appeared to have more drought tolerance. The greater density of root system contributed to the drought resistance.

During the period of May through October the new variety grass was regularly mown at intervals of 7–10 days and produced none or extremely few seed heads. The closest known variety of grass in the same test area under the same mowing conditions produced many seed heads.

Continued asexual reproduction by stolons and rhizomes have confirmed that the above described characteristics are transmitted through succeeding propagations and have confirmed that the plant has the following unique combination of characteristics:

(a) An attractive deep-green-color;

(b) The grass is low growing and erect in habit;

(c) The grass spreads by stolons and rhizomes forming a dense uniform turf surface with an extensive root system;

(d) Culms vary in height from 8–25 cm.;

(e) Leaves are folded in bud shoot;

(f) The blade is V-shaped in cross section with the upper leaf blade surface deeply ridged;

(g) The blades are slender and gradually taper to an acute point;

(h) The first mature leaf is 3–4 millimeters in width and 35–100 millimeters in length;

(i) The blade is glabrous except at the base near the ligule where from 3–8 hairs are present along the outer edge of the blade;

(j) The ligule is membranous, acute and of medium height;

(k) Auricles are absent;

(l) The collar is broad and somewhat restricted with its midvein slightly visible;

(m) The collar is glabrous except at edges where 1–3 hairs are present;

(n) The sheath is split (margins generally overlapping), glabrous (except near ligule) and compressed;

(o) The entire plant is glabrous except in the ligule area. Hairs are connected in two places (1) on the inside of the collar at the base of the ligule where 5–12 hairs are connected and (2) where the ligule sheath and collar meet where 10–15 hairs exist on each side;

(p) The internodal spaces on the stolons are 2–4.5 centimeters and on the culms the internodal spaces are 2–4 centimeters apart;

(q) Inflorescence consists of 2 paired spikes at the top of the main stem deflexed at maturity, from 25–30 millimeters long;

(r) The spikelets are glabrous, in two rows 2–3 millimeters long, blunt at their base, pointed at their tips, born singly on short branches, and glumes are present;

(s) The spikelets are sterile, 3 stamens, 2 styles when present.

DESCRIPTION OF CLOSEST KNOWN VARIETY OF THE SPECIES

By comparison, the closest known variety of the species is described and claimed in my plant patent application Ser. No. 466,265 filed May 2, 1974 on a *Paspalum Vaginatum* Grass Plant. Reference to the "other *Paspalum vaginatum*" grass in the above description refers to the grass plant described in my application Ser. No. 466,265.

By comparison, the closest known variety of the species (application Ser. No. 466,265) is low growing, erect in habit, culms vary in height from 12–43 centimeters, the first mature leaf is 2–4 millimeters in width, 80–120 millimeters in length, the blade is also glabrous except at base near ligule. The ligule is truncate to extremely acute. The collar is broad, distinct, and glabrous. The sheath is split (margins generally overlapping then opening again near node). In the ligule area only a few hairs are connected. The internodal space on the stolons are 5–7 centimeters.

The claimed *Paspalum vaginatum* grass plant is illustrated in the accompanying color photographs with photographs of the closest known *Paspalum vaginatum* grass plant, that is of my application Ser. No. 466,265. The most noticeable variations between the two grasses occur when the grasses are mown down to about ⅜ inches in height and the appearance of the two surfaces are then quite distinctly different; specifically, the new variety has a more dense leaf intertwining structure, the new variety has a deeper green color, the new variety shows no seed heads after mowing under regular turf grass lawn mowing conditions and showed and produced fewer seed heads when not regularly mown.

In the drawings: FIG. 1 is a photograph showing side views of pots containing the new variety of grass and the closest known variety grass (identified by prior art and referring to grass of application Ser. No. 466,265), both grasses being taken from the same test area and potted at the same time, and further showing, both grasses being in unmown or uncut condition, the few seed heads formed on the new variety as compared to the profuse production of seed head on the closest known variety, the finer leaf texture of the closest known variety as compared with the somewhat broader leaf texture of the new variety, and greater density of the new variety as compared to the more open growth pattern of the closest known variety.

Figure 4:
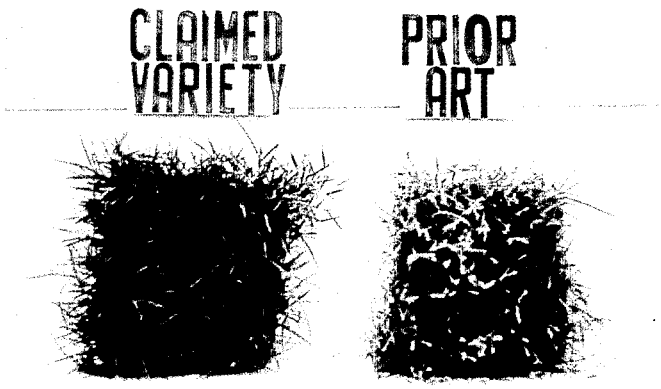

FIG. 4 is a top view of sod pieces from the same test area of the new grass variety and the closest known grass variety, which sod pieces have been subjected to the same mowing conditions at virtually the same time, and show the greater density of the new grass variety, the lack of seed heads on the new variety grass, the entwining nature of the leaves of the new variety grass, the profusion of seed heads on the closest known variety grass, the finer leaf and more open texture of the closest known variety grass, and the more upright leaf growth habit of the closest known variety grass.

Figure 1:
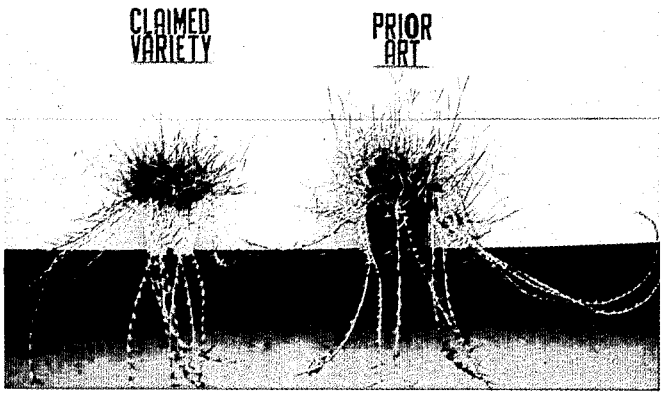
Figure 2:
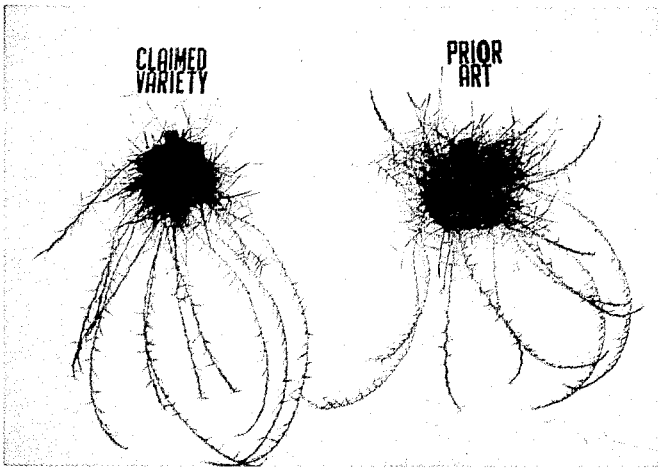
FIG. 2 is a photograph showing top views of the potted grass of FIG. 1 and further showing density of the new variety as compared with the more open and less entwining characteristic of the closest known variety.
Figure 3:
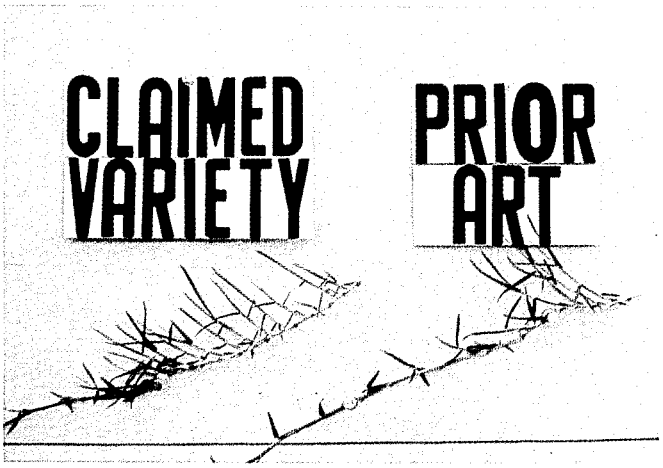
FIG. 3 is a photograph of a stolon of the new variety of grass and a stolon of the closest known variety grass and showing numerous leaves on the stolons of the claimed variety and the relatively few leaves on the closest known variety.
Figure 5:
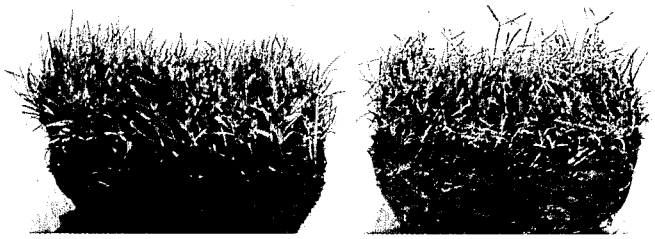

FIG. 5 is a side view of sod pieces (not the identical sod pieces of FIG. 4) from the same test area of the new grass variety and the closest known grass variety, which sod pieces have been also subjected to the same mowing conditions at virtually the same time, the sod pieces being photographed about 5 days after having been mown and showing the characteristics of the grass varieties as stated in the description of FIG. 4.

Having now described the new and distinct variety of *Paspalum vaginatum* grass plant which I have discovered and asexually reproduced, I claim:

1. A new variety of *Paspalum vaginatum* grass plant herein shown and described characterized by: dense uniform intertwining low growing leaves of grass spreading by stolons and rhizomes; in unmown condition the grass plant producing few seed heads, in regular periodic mowing conditions (7–10 days) virtually no seed heads are produced between mowing whereby a low growing dense turf grass surface is established without seed heads, increased resistance and tolerance to drought and cold.

No references cited.

ROBERT E. BAGWILL, Primary Examiner